US012167829B2

(12) United States Patent
Nielsen et al.

(10) Patent No.: US 12,167,829 B2
(45) Date of Patent: Dec. 17, 2024

(54) IMAGE CAPTURE SELECTION

(71) Applicant: AMBU A/S, Ballerup (DK)

(72) Inventors: Brian Nielsen, Næstved (DK); Tai Chi Minh Ralph Eastwood, Glostrup (DK)

(73) Assignee: AMBU A/S, Ballerup (DK)

( * ) Notice: Subject to any disclaimer, the term of this patent is extended or adjusted under 35 U.S.C. 154(b) by 146 days.

(21) Appl. No.: 17/786,490

(22) PCT Filed: Dec. 15, 2020

(86) PCT No.: PCT/EP2020/086131
§ 371 (c)(1),
(2) Date: Jun. 16, 2022

(87) PCT Pub. No.: WO2021/122536
PCT Pub. Date: Jun. 24, 2021

(65) Prior Publication Data
US 2023/0025755 A1      Jan. 26, 2023

(30) Foreign Application Priority Data

Dec. 19, 2019   (DK) .............................. PA201970799

(51) Int. Cl.
*A61B 1/00*        (2006.01)
*A61B 1/045*       (2006.01)
(Continued)

(52) U.S. Cl.
CPC .... *A61B 1/000095* (2022.02); *A61B 1/00042* (2022.02); *H04N 23/633* (2023.01);
(Continued)

(58) Field of Classification Search
None
See application file for complete search history.

(56) References Cited

U.S. PATENT DOCUMENTS 6,533,721 B1 *   3/2003   Beutter ................ H04N 23/673
                                                              348/E5.045
6,549,643 B1     4/2003   Toklu et al.
(Continued)

FOREIGN PATENT DOCUMENTS

EP        1625751 A2    2/2006
EP        1500367 B1    3/2008
(Continued)

OTHER PUBLICATIONS

International Search Report and Written Opinion in PCT/EP2020/086131 dated Mar. 12, 2021, 11 pages.
(Continued)

*Primary Examiner* — Hung Q Dang
(74) *Attorney, Agent, or Firm* — Faegre Drinker Biddle & Reath LLP

(57) ABSTRACT

Disclosed is a method for operating an endoscope system and an endoscope system comprising an image sensor and a processing device, the image sensor comprising an image sensor output, the processing device comprising an input connected to the image sensor output. The method comprising: consecutively receiving frames captured by the image sensor; receiving a first capture signal, indicative of an operator performing a first action associated with capturing a still image of the frames captured by the image sensor; storing a first plurality of frames of the frames captured by the image sensor; determining one or more quality properties of each of the first plurality of frames; and selecting a designated frame of the first plurality of frames based on the one or more quality properties.

20 Claims, 3 Drawing Sheets

(51) Int. Cl.
  *H04N 23/50*  (2023.01)
  *H04N 23/63*  (2023.01)
  *H04N 23/68*  (2023.01)
  *H04N 23/951*  (2023.01)

(52) U.S. Cl.
  CPC ......... *H04N 23/683* (2023.01); *H04N 23/951* (2023.01); *H04N 23/555* (2023.01)

(56) References Cited

U.S. PATENT DOCUMENTS

| | | | |
|---|---|---|---|
| 6,717,609 | B2 | 4/2004 | Sugimoto et al. |
| 7,048,685 | B2 | 5/2006 | Sakiyama |
| 7,184,100 | B1 | 2/2007 | Wilf et al. |
| 7,492,388 | B2 | 2/2009 | Odlivak et al. |
| 7,534,205 | B2 | 5/2009 | Wiklof |
| 7,869,856 | B2 | 1/2011 | Refael |
| 7,995,045 | B2 | 8/2011 | Dunki-Jacobs |
| 8,199,188 | B2 | 6/2012 | Amling et al. |
| 8,199,813 | B2 | 6/2012 | Bendall et al. |
| 8,253,785 | B2 | 8/2012 | Abe |
| 8,723,935 | B2 | 5/2014 | Kouno |
| 9,007,450 | B2 | 4/2015 | Amling et al. |
| 9,030,543 | B2 | 5/2015 | Tsuyuki et al. |
| 9,084,529 | B2 | 7/2015 | Saito |
| 9,167,160 | B2 | 10/2015 | King |
| 9,289,113 | B2 | 3/2016 | Ozawa |
| 9,332,890 | B2 | 5/2016 | Ozawa |
| 9,672,619 | B2 | 6/2017 | Yaguchi |
| 9,740,939 | B2 | 8/2017 | Yaguchi |
| 9,913,575 | B2 | 3/2018 | Gazdzinski |
| 10,004,389 | B2 | 6/2018 | Shigeta |
| 10,028,645 | B2 | 7/2018 | Gazdzinski |
| 10,028,646 | B2 | 7/2018 | Gazdzinski |
| 10,250,853 | B2 | 4/2019 | Yanagidate |
| 10,980,397 | B1 | 4/2021 | Ubbesen |
| 11,074,690 | B2 | 7/2021 | Jørgensen |
| 11,096,553 | B2 | 8/2021 | Sonnenborg |
| 2003/0120156 | A1* | 6/2003 | Forrester ................ A61B 1/042 600/473 |
| 2005/0129108 | A1 | 6/2005 | Bendall et al. |
| 2005/0219666 | A1 | 10/2005 | Ejima et al. |
| 2006/0015008 | A1 | 1/2006 | Kennedy |
| 2007/0013771 | A1 | 1/2007 | Imaizumi et al. |
| 2007/0078300 | A1 | 4/2007 | Zinaty et al. |
| 2007/0156021 | A1 | 7/2007 | Morse et al. |
| 2007/0222865 | A1 | 9/2007 | Levien et al. |
| 2008/0058593 | A1 | 3/2008 | Gu et al. |
| 2008/0122924 | A1 | 5/2008 | Tashiro |
| 2009/0105544 | A1 | 4/2009 | Takahira |
| 2009/0109431 | A1 | 4/2009 | Delmonico et al. |
| 2009/0251549 | A1* | 10/2009 | Meguro ................... G03B 5/00 348/208.4 |
| 2010/0165088 | A1 | 7/2010 | Seo |
| 2011/0282142 | A1 | 11/2011 | Refael |
| 2011/0290887 | A1 | 12/2011 | Wang et al. |
| 2012/0057009 | A1 | 3/2012 | Liao et al. |
| 2012/0113239 | A1 | 5/2012 | Krupnik et al. |
| 2012/0238810 | A1* | 9/2012 | Kobayashi ............. A61B 5/061 600/109 |
| 2012/0307039 | A1 | 12/2012 | Holmes |
| 2014/0132746 | A1* | 5/2014 | King ....................... H04N 1/215 348/208.6 |
| 2014/0221749 | A1 | 8/2014 | Grant et al. |
| 2015/0164482 | A1* | 6/2015 | Toji ....................... A61B 8/5276 600/443 |
| 2015/0208900 | A1 | 7/2015 | Vidas et al. |
| 2015/0320299 | A1 | 11/2015 | Krupnik |
| 2016/0128545 | A1 | 5/2016 | Morita |
| 2016/0210411 | A1 | 7/2016 | Mentis |
| 2016/0335751 | A1 | 11/2016 | Sidar et al. |
| 2017/0034484 | A1 | 2/2017 | Yanagidate |
| 2017/0085831 | A1* | 3/2017 | Hashimoto ........... A61B 1/0002 |
| 2017/0143310 | A1* | 5/2017 | Funakubo ............. A61B 8/465 |
| 2017/0215720 | A1 | 8/2017 | Walker et al. |
| 2017/0290571 | A1* | 10/2017 | Funakubo ................ A61B 8/54 |
| 2017/0374275 | A1 | 12/2017 | Shimokura et al. |
| 2018/0199795 | A1 | 7/2018 | Maruyama et al. |
| 2018/0268523 | A1 | 9/2018 | Takahasi et al. |
| 2018/0310802 | A1 | 11/2018 | Gilreath et al. |
| 2019/0052854 | A1* | 2/2019 | Kojima ............... A61B 1/00042 |
| 2020/0184644 | A1 | 6/2020 | Ueda |
| 2020/0305700 | A1 | 10/2020 | Kamon |
| 2021/0259517 | A1 | 8/2021 | Ubbesen |

FOREIGN PATENT DOCUMENTS

| | | | |
|---|---|---|---|
| EP | 2168496 | A1 | 3/2010 |
| EP | 1870827 | B1 | 4/2010 |
| EP | 2054852 | B1 | 6/2010 |
| EP | 1550311 | B1 | 8/2011 |
| EP | 2053862 | B1 | 1/2014 |
| EP | 2823749 | A1 | 1/2015 |
| EP | 1743568 | B1 | 8/2015 |
| EP | 2926717 | A1 | 10/2015 |
| EP | 2994033 | A1 | 3/2016 |
| EP | 3020322 | A1 | 5/2016 |
| EP | 3050484 | A1 | 8/2016 |
| EP | 2733924 | B1 | 4/2017 |
| EP | 3297515 | A1 | 3/2018 |
| EP | 2868254 | B1 | 4/2018 |
| EP | 3384460 | A1 | 10/2018 |
| JP | H-11339006 | A | 12/1999 |
| WO | WO-2015067750 | A1* | 5/2015 ............. H04N 5/232 |
| WO | 2016187124 | A1 | 11/2016 |
| WO | 2017094535 | A1 | 6/2017 |
| WO | 2018117468 | A1 | 6/2018 |
| WO | 2019039252 | A1 | 2/2019 |
| WO | 2019/130964 | A1 | 7/2019 |
| WO | 2019/216084 | A1 | 11/2019 |

OTHER PUBLICATIONS

First technical examination report in Danish patent application PA 2019 70799 dated May 15, 2020, 10 pages.
Second technical examination report in Danish patent application No. PA 2019 70799 dated Oct. 15, 2020, 5 pages.

* cited by examiner

IMAGE CAPTURE SELECTION

CROSS-REFERENCE TO PRIOR APPLICATION

This application is a § 371 National Stage Application of PCT International Application No. PCT/EP2020/086131 filed Dec. 15, 2020, which claims the priority of Danish Patent Application No. PA201970799, filed Dec. 19, 2019, each of which are herein incorporated by reference in their entirety.

The present disclosure relates to an endoscope and an endoscope system, more specifically to a method and an endoscope system configured to capture a still image of enhanced quality.

BACKGROUND

A video feed, e.g. comprising a plurality of frames, from an endoscope may in some instances be transmitted to a processing device, sometimes referred to as a monitor, having an output, e.g. HDMI or SDI, which allow transmission of the received video feed to an external device, such as a video-/image-grabber or an external display, such as a HD-display. A user may choose to grab a still image or a sequence of frames from the video feed by using an external device, such as a video-/image-grabber connected to an output port of the monitor of the endoscope system.

Although, the processing device may do image processing on the video feed and/or frames received from the endoscope, e.g. by applying various filters to the frames and/or video feed and output a processed video feed and/or frames as the output to external devices, in the context of the present disclosure a video feed and/or frames received from the endoscope are referred to as the same video feed and/or frame regardless of having been subject to image processing.

The processing device and/or an external video-/image-grabber may further allow capturing of still images of the received video feed, e.g. by a push of a control button.

SUMMARY

It is an object of the present disclosure to provide a solution which at least improve the solutions of the prior art.

It is a further object of the present disclosure to provide a system and method facilitating enhanced quality of captured still images, as well as providing for enhanced output of captured still images.

Accordingly, an endoscope system is disclosed, such as an endoscope system comprising an image sensor and a processing device. The image sensor comprises an image sensor output. The processing device comprises an input connected to the image sensor output. The input of the processing device may be connected to the image sensor output by a wireless connection.

The processing device is configured to: receive, such as consecutively receive, at a first frame rate, via the input, frames captured by the image sensor; receive a first capture signal indicative of an operator performing a first action associated with capturing a still image of the frames received via the input; store, such as temporarily store, a first plurality of frames of the frames received via the input; determine one or more quality properties of each of the first plurality of frames; and select a designated frame of the first plurality of frames based on the one or more quality properties.

Also disclosed is a method for operating an endoscope system, such as the disclosed endoscope system, such as an endoscope system comprising an image sensor and a processing device.

The method comprises: consecutively receiving frames captured by the image sensor; receiving a first capture signal, indicative of an operator performing a first action associated with capturing a still image of the frames captured by the image sensor; storing a first plurality of frames of the frames captured by the image sensor; determining one or more quality properties of each of the first plurality of frames; and selecting a designated frame of the first plurality of frames based on the one or more quality properties.

It will be understood that the frames received may not be the raw input captured by the image sensor electronics but may have been subject to some initial image processing prior to being received.

The one or more quality properties may comprise one or more of sharpness, contrast, and noise. The processing device may be configured to perform a Laplacian operation and/or a Laplacian of Gaussian operation to determine the one or more quality properties of each of the first plurality of frames.

The first plurality of frames may be stored, such as temporarily stored, after receipt of the first capture signal. For example, the first plurality of frames may be stored in response to receipt of the first capture signal. For example, the first plurality of frames may be frames received via the input after receiving the first capture signal and/or captured by the image sensor after receiving the first capture signal. Storing a plurality of frames received via the input after receiving the first capture signal provides for a simple solution avoiding the need for continuously storing captured images for later selection in a buffer.

The first action may correspond to the operator initiating a press of a capture button. Thus, the first capture signal may be indicative of the operator pressing the capture button. For example, the first action may correspond to the operator initiating the press of the capture button, such as a press down on the capture button. Thus, the first capture signal may be indicative of the operator providing a press down on the capture button.

After selection of the designated frame of the first plurality of frames, the first plurality of frames, e.g. except the designated frame, may be deleted or discarded.

A second capture signal may be received after receipt of the first capture signal. For example, the processing device may be configured to receive a second capture signal after receipt of the first capture signal. The second capture signal may be indicative of the operator performing a second action associated with capturing the still image of the frames received via the input. For example, the second action may correspond to the operator releasing the press of the capture button.

The first plurality of frames may be stored, such as temporarily stored, after receipt of the second capture signal. For example, the first plurality of frames may be stored in response to receipt of the second capture signal. For example, the first plurality of frames may be frames received via the input after receiving the second capture signal.

The first plurality of frames may comprise frames received via the input between receipt of the first capture signal and receipt of the second capture signal. The first plurality of frames may consist of frames received via the input between receipt of the first capture signal and receipt of the second capture signal.

The first plurality of frames may be a first number of frames. The first number of frames may be more than 5 frames, such as 10 frames. The first frame rate may be between 20-40 frames per second (fps), such as 30 fps. The first number of frames may correspond to a time span of between 200-500 ms, such as between 300-350 ms, such as approximately 333 ms.

In accordance with more than the first number of frames being received via the first input between receipt of the first capture signal and receipt of the second capture signal, the first plurality of frames may consist of the first number of frames received via the first input immediately prior to receipt of the second capture signal. Thus, in case the time between the first capture signal and the second capture signal is more than the time span of the first number of frames, the first plurality of frames may be selected to be the frames received up to the time of receipt of the second capture signal.

Alternatively, in accordance with more than the first number of frames being received via the first input between receipt of the first capture signal and receipt of the second capture signal, the first plurality of frames may consist of the first number of frames received via the first input immediately after receipt of the first capture signal. Thus, in case the time between the first capture signal and the second capture signal is more than the time span of the first number of frames, the first plurality of frames may be selected to be the frames received immediately after the time of receipt of the first capture signal.

In accordance with less than the first number of frames being received via the first input between receipt of the first capture signal and receipt of the second capture signal, the first plurality of frames may consist of the first number of frames received via the first input after receipt of the first capture signal. Hence, collection of frames to store, such as temporarily store, as the first plurality of frames may be continued after receipt of the second capture signal, in case the time between the first capture signal and the second capture signal is less than the time span needed to receive the first number of frames.

The designated frame may be output via a first output. The processing device may comprise the first output. The first output may be configured to be connected to an external image processing device, such as a video grabber. The processing device may be configured to output the designated frame via the first output. Thereby, the processing device may be configured to output the best available frame of the first plurality of frames via the first output.

The frames received via the input and/or captured by the image sensor may be output via the first output and/or a second output. The processing device may comprise a second output. The second output may be configured to be connected to an external display device, such as an external monitor or HD-display. The processing device may be configured to output, via the second output, the frames received via the input. Thus, the output provided via the second output may be substantially a relay of the frames received and captured by the image sensor. However, it will be understood that in outputting the frames received via the input some image processing may be performed on the received frames in order to output comprehensible frames.

Prior to receiving the first capture signal and/or the second capture signal, the frames received via the input and/or captured by the image sensor may be output via the first output and/or via the second output. After receipt of the first capture signal and/or the second capture signal, such as in response to receiving the first capture signal and/or the second capture signal, the designated frame may be output, such as continuously and/or repeatedly output, via the first output, and/or the frames captured by the image sensor may be output via the second output.

The processing device may be configured to change between a first state and a second state, such as from the first state to the second state. The processing device may be configured to change from the first state to the second state after receipt of the first capture signal and/or after receipt of the second capture signal, such as in response to receipt of the first capture signal and/or in response to receipt of the second capture signal.

In the first state the processing device may be configured to output, via the first output, the frames received via the input. Thus, the output provided via the first output, when the processing device is in the first state, may be substantially a relay of the frames received and captured by the image sensor. However, it will be understood that in outputting the frames received via the input some image processing may be performed on the received frames in order to output comprehensible frames.

In the second state the processing device may be configured to output, e.g. continuously output and/or repeatedly output, via the first output, the designated frame. Thereby, a "best" frame may be provided to an external device, e.g. for storing in a central image database.

In the first state the processing device may be configured to output, via the second output, the frames received via the input. In the second state the processing device may be configured to output, via the second output, the frames received via the input. For example, the processing device may be configured to output, via the second output, the frames received via the input, regardless of whether the processing device is in the first state or in the second state. Thus, continuous performance of the procedure may be allowed while providing a designated frame to an external device, e.g. for storing in a central image database.

The processing device may be configured to change from the second state to the first state after a predetermined time after changing from the first state to the second state. The predetermined time may be more than 5 seconds. The predetermined time may be less than 30 seconds. The predetermined time may be between 5-20 seconds, such as 5 seconds or 10 seconds.

The processing device may be configured to change from the second state to the first state in response to receipt of a third capture signal, e.g. indicative of an operator performing a third action. The third action may correspond to the operator initiating a second press of the capture button, such as a second press down on the capture button. Thus, the third capture signal may be indicative of the operator providing a second press down on the capture button, e.g. after receipt of the first and/or second capture signal and/or after the operator has performed the first and/or second action. Alternatively, the third action may correspond to the operator initiating an input on the capture button in another direction, e.g. a perpendicular direction, than the direction of the input on the capture button corresponding to the first and/or second actions.

The endoscope system may comprise a display unit. The processing device may be configured to display the designated frame via the display unit. The processing device may be configured to display the frames received via the input concurrently with display of the designated frame.

The endoscope system may comprise an endoscope. The endoscope may have an endoscope handle and an elongated flexible member extending from the endoscope handle to a distal end. The image sensor may be positioned at the distal end. Alternatively, the image sensor may be positioned distant from the distal end, e.g. in the handle, and fibreoptic in the elongated flexible member may allow transmission of light from the distal end of the elongated flexible member to the image sensor.

The processing device may be configured to store the designated frame to a memory, e.g. to an internal memory of the processing device and/or to an external memory. For example, the processing device may be configured to cause storing of the designated frame to an external memory. For example, the processing device may issue a signal to an external device, such as an image grabber, to cause the external device to store the designated frame.

It is an advantage of the disclosure that it makes it easier for the user to grab still images and reduces the need for repeatably recapturing a still image because of bad image quality, such as blurring, which may be caused, e.g. by movement of the camera.

It is a further advantage of the disclosure that an enhanced quality image may be provided to certain external devices, while a live image view may be preserved via another connected device.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1:
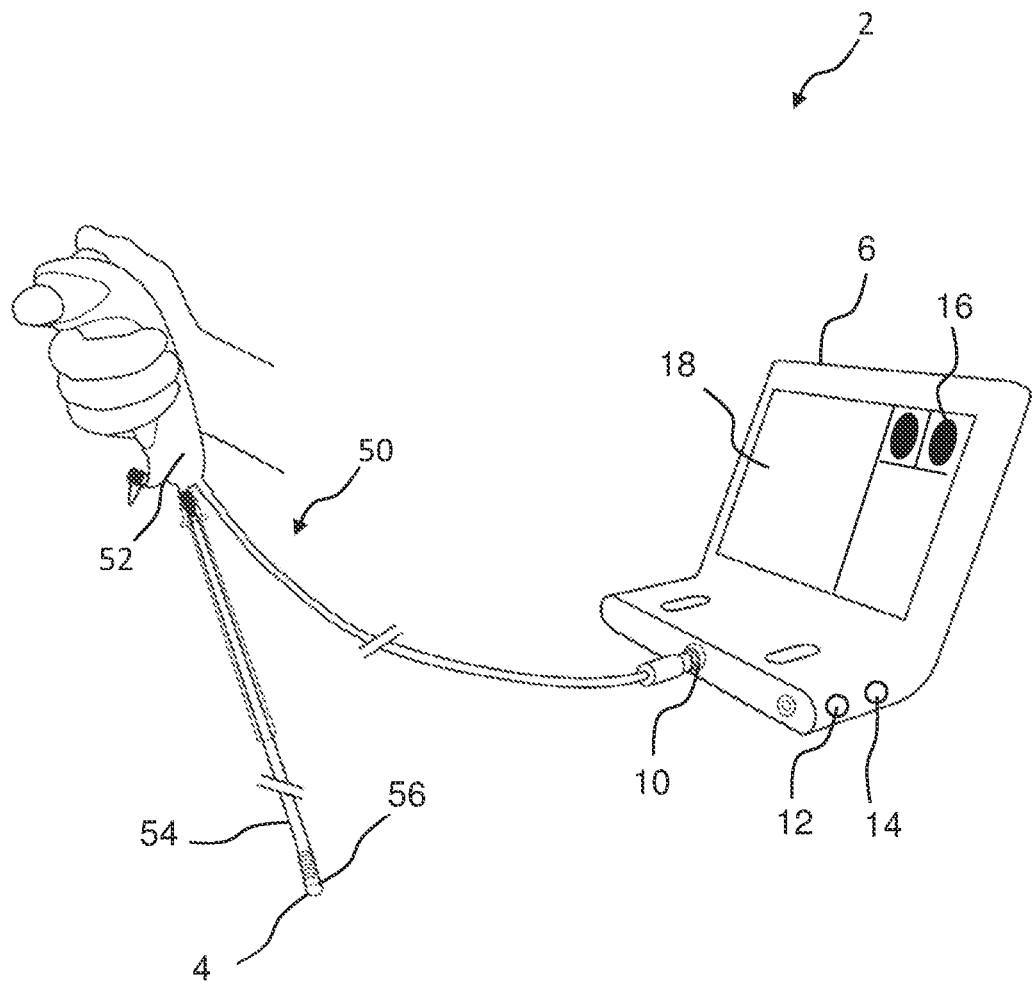
FIG. 1 schematically illustrates an exemplary endoscope system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the disclosure or as a limitation on the scope of the disclosure. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 2:
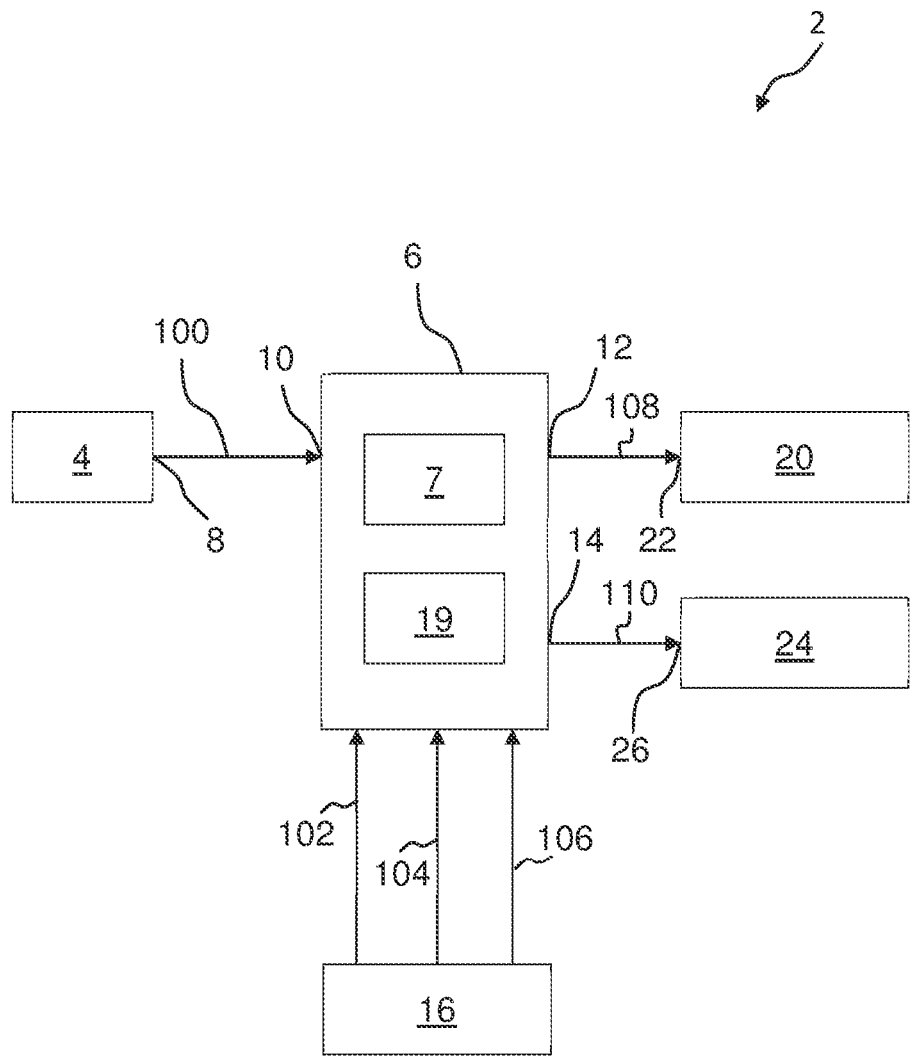
FIG. 2 is a block diagram of an exemplary endoscope system.

FIG. 1 schematically illustrates an exemplary endoscope system 2, and FIG. 2 is a block diagram of the exemplary endoscope system 2. The endoscope system 2 comprises an image sensor 4 and a processing device 6.

The image sensor 4 may be a digital camera unit, e.g. positioned at a distal end 56 of an elongated member 54 of an endoscope 50, as illustrated in FIG. 1. Alternatively, the image sensor 4 may be positioned in an endoscope handle 52 of the endoscope 50 and be optically coupled, e.g. via optical fibres, to the distal end 56 of the elongated member 54. The elongated member 54 may be flexible to facilitate conformation to the internal cavity wherein it is used.

The image sensor 4 comprises an image sensor output 8. The processing device 6 comprises an input 10. The input 10 is connected to the image sensor output 8. The processing device 6 comprises a processing unit 7, e.g. comprising a CPU, GPU or FPGA. The processing device 6 comprises memory 19.

The endoscope system comprises a display unit 18. The display unit 18 may form part of the processing device 6, as illustrated. The display unit 18 may be a touch sensitive display.

The processing device 6 comprise a first output 12 and a second output 14. The first output 12 may be configured to be connected to an external image processing device 20, such as a video grabber. The second output 14 may be configured to be connected to an external display device 24.

The endoscope system 2 comprises a capture button 16 configured to receive an operator input, such as a touch input. The capture button 16 may be a soft button provided on a touch sensitive display 18 of the processing device 6. Alternatively or additionally, a capture button may be provided on the endoscope handle 52 of the endoscope 50.

The processing device 6 is configured to receive a frame 100 of a video feed from the image sensor 4 via the input 10. For example, the processing device 6 may consecutively receive, e.g. at a first frame rate, via the input 10, frames 100 captured by the image sensor 4. The frames 100 may form a video feed. The frames 100 and/or the video feed may form part of an input signal.

The processing device 6 is further configured to receive a first capture signal 102, e.g. indicative of an operator performing a first action associated with capturing a still image of the received frames 100.

The first capture signal 102 may be received from the capture button 16. The processing device 6 may further receive a second capture signal 104, e.g. indicative of an operator performing a second action associated with capturing the still image of the received frames 100. The second capture signal 104 may be configured to be received after receipt of the first capture signal 102. For example, the first action may correspond to a press (e.g. down press) of the capture button 16 and the second action may correspond to release of the press on the capture button 16.

The processing device 6 is configured to store, such as temporarily store, e.g. in the memory 19, a first plurality of frames, e.g. five frames or 10 frames, of the frames 100 received via the input 10. The first plurality of frames may be stored after receipt of the first capture signal 102, e.g. the first plurality of frames may be stored in response to receipt of the first capture signal 102, e.g. receipt of the first capture signal 102 may trigger storing of a first plurality of frames. The first plurality of frames may be frames received via the input after receiving the first capture signal 102. For example, the first plurality of frames may comprise, or consist of, frames received via the input 8 between receipt of the first capture signal 102 and receipt of the second capture signal 104.

The processing device 6, such as the processing unit 7, is configured to determine one or more quality properties of each of the first plurality of frames and select a designated frame of the first plurality of frames based on the one or more quality properties. The one or more quality properties may be sharpness, contrast, and/or noise.

The processing device 6 may cause storing of the designated frame to an external memory (not shown).

The processing device 6 may be configured to output a first output signal 108 via the first output 12, e.g. to the connected external image processing device 20. The first output signal 108 may comprise the designated frame. The processing device 6 may be configured to output a second output signal 110, via the second output 14. The second output signal 110 may comprise the frames 100 received via the input. For example, the second output signal 110 may substantially correspond to the video feed and/or the input signal received from the image sensor 4.

The processing device 6 may be configured to change between a first state and a second state, e.g. in response to receipt of the first capture signal 102 and/or the second capture signal 104. For example, the processing device 6 may be configured to change from the first state to the second state after, such as in response to, receipt of the first capture signal 102 and/or the second capture signal 104. In the first state the processing device 6 may be configured to output, via the first output 12, the frames 100 received via the input 10, and in the second state the processing device 6 is configured to output, via the first output 12, the designated frame. Thus, the output signal 108 via the first output 12 may change based on user input, e.g. based on receipt of the first capture signal 102 and/or receipt of the second capture signal 104.

The processing device 6 may be configured to output, via the second output 14, the frames 100 received via the input 10, both in the first state and in the second state. Thus, the output signal 110 via the second output 14 may be unaffected by the receipt of the first capture signal 102 and/or receipt of the second capture signal 104.

The processing device 6 may be configured to change back to the first state, e.g. from the second state to the first state, after a predetermined time after changing from the first state to the second state. Alternatively, or additionally, the processing device 6 may be configured to change back to the first state, e.g. from the second state to the first state, in response to receipt of a third capture signal 106, e.g. from the capture button 16 (e.g. a press down on the capture button 16, while the processing device is in the second state) or alternatively from another button. The third capture signal 106 may be indicative of an operator performing a third action. Thus, upon receipt of the third capture signal 106, the processing device 6 may be configured to change back to the first state, wherein the first output signal 108 of the first output 12 and the second output signal 110 of the second output 14 corresponds to the frames 100 received via the input 10.

The processing device 6 may be configured to display the designated frame via the display unit 18, e.g. in the first state and/or in the second state. The processing device 6 may be configured to display the frames 100 received via the input 10 concurrently with display of the designated frame. For example, the designated frame may be shown in a first portion of the display unit 18 and the frames 100 received via the input 10 may be displayed in a second portion of the display unit 18.

Figure 3:
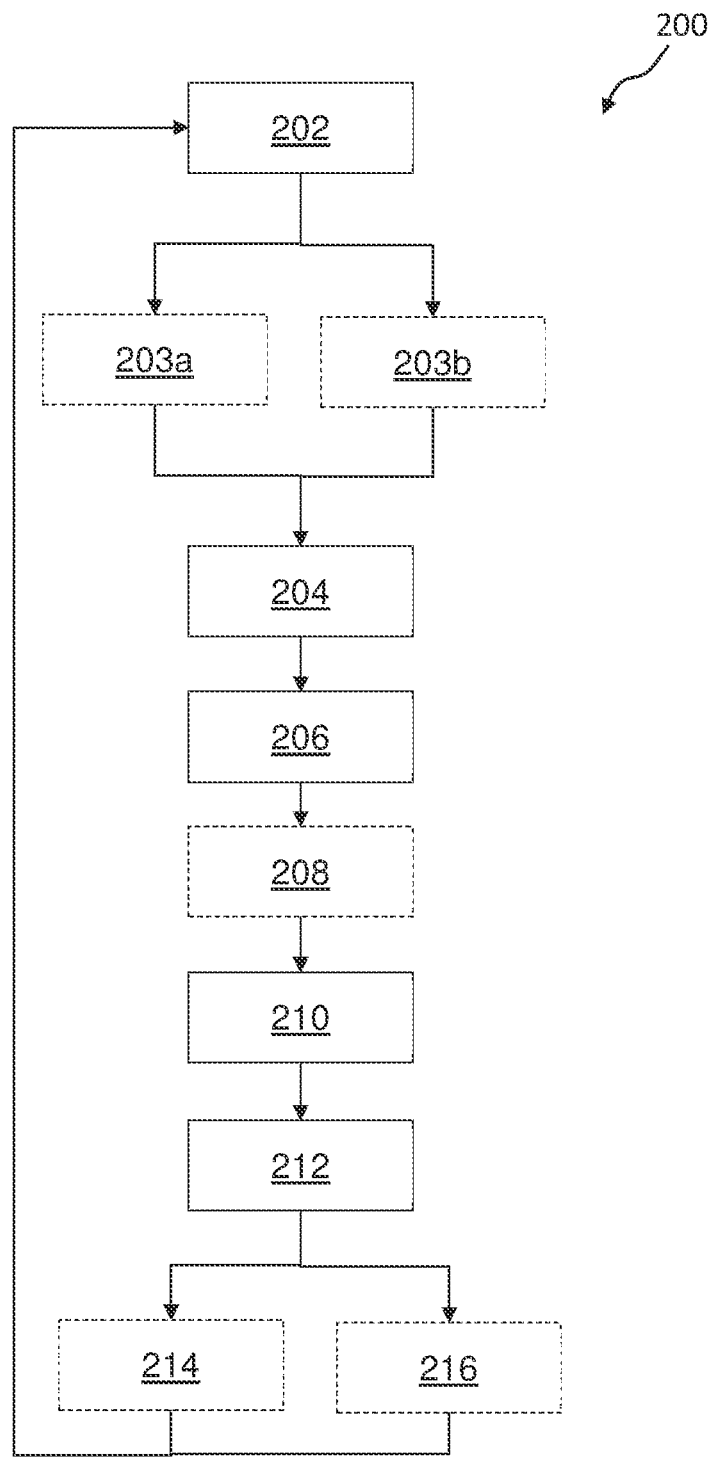
FIG. 3 is a block diagram of an exemplary method.

FIG. 3 is a block diagram of an exemplary method 200 for operating an endoscope system, such as the endoscope system as described with respect to FIGS. 1 and 2, e.g. an endoscope system comprising an image sensor and a processing device.

The method 200 comprises receiving 202, such as consecutively receiving, frames captured by the image sensor.

The method 200 comprises receiving 204 a first capture signal. The first capture signal may be indicative of an operator performing a first action associated with capturing a still image of the frames captured by the image sensor.

The method 200 comprises storing 206 a first plurality of frames of the frames captured by the image sensor. Storing 206 the first plurality of frames may be performed after receipt 204 of the first capture signal, e.g. in response to receipt 204 of the first capture signal. Thus, the first plurality of frames may be frames captured by the image sensor after receiving 204 the first capture signal.

The method 200 optionally comprises receiving 208 a second capture signal. The second capture signal may be indicative of an operator performing a second action associated with capturing the still image of the frames captured by the image sensor.

The method 200 comprises determining 210 one or more quality properties of each of the first plurality of frames. Determining 210 the one or more quality properties may be performed in response to receipt 208 of the second capture signal. Alternatively, determining 210 the one or more quality properties may be performed in response to a predetermined number of frames being stored 206.

The method 200 comprises selecting 212 a designated frame of the first plurality of frames based on the one or more quality properties. For example, the designated frame may be the frame of the first plurality of frames having a highest quality score, such as less noise, highest contrast, or similar. The quality score may be a combination of several factors.

The method 200 optionally comprises outputting 214 the designated frame via a first output. The designated frame may be output 214 via the first output after receipt 204 of the first capture signal and/or after receipt 208 of the second capture signal. For example, the designated frame may be output 214 via the first output in response to receipt 204 of the first capture signal and/or in response to receipt 208 of the second capture signal.

The method 200 optionally comprises outputting 216 the frames captured by the image sensor via a second output. The designated frame may be output 214 via the first output simultaneously with the frames captured by the image sensor being output 216 via the second output.

Prior to receiving 204 the first capture signal, the method 200 optionally comprises outputting 203a, via the first output, the frames captured by the image sensor, and outputting 203b, via the second output, the frames captured by the image sensor. Thus, prior to receiving 204 the first capture signal, the method 200 may comprise outputting the frames captured by the image sensor on both the first output and the second output.

Exemplary systems and methods are disclosed in the following items:

1. An endoscope system comprising an image sensor and a processing device, the image sensor comprising an image sensor output, the processing device comprising an input connected to the image sensor output, the processing device is configured to:
   consecutively receive at a first frame rate, via the input, frames captured by the image sensor;
   receive a first capture signal, indicative of an operator performing a first action associated with capturing a still image of the frames received via the input;
   store a first plurality of frames of the frames received via the input;
   determine one or more quality properties of each of the first plurality of frames; and
   select a designated frame of the first plurality of frames based on the one or more quality properties.

2. Endoscope system according to item 1, wherein the first plurality of frames is stored after receipt of the first capture signal, and wherein the first plurality of frames are frames received via the input after receiving the first capture signal.

3. Endoscope system according to any of the preceding items, wherein the first action corresponds to the operator initiating a press of a capture button.

4. Endoscope system according to any of the preceding items, wherein the processing device is configured to receive a second capture signal after receipt of the first capture signal, wherein the second capture signal is indicative of the operator performing a second action associated with capturing the still image of the frames received via the input.

5. Endoscope system according to item 4 as dependent on item 3, wherein the second action corresponds to the operator releasing the press of the capture button.

6. Endoscope system according to any of items 4-5, wherein the first plurality of frames comprises frames received via the input between receipt of the first capture signal and receipt of the second capture signal.

7. Endoscope system according to any of the preceding items, wherein the first plurality of frames is a first number of frames, optionally wherein the first number of frames are more than 5 frames, such as 10 frames.

8. Endoscope system according to item 7 as dependent on any of items 4-6, wherein, in accordance with more than the first number of frames being received via the first input between receipt of the first capture signal and receipt of the second capture signal, the first plurality of frames consists of the first number of frames received via the first input immediately prior to receipt of the second capture signal.

9. Endoscope system according to any of items 7-8 as dependent on any of items 4-6, wherein, in accordance with less than the first number of frames being received via the first input between receipt of the first capture signal and receipt of the second capture signal, the first plurality of frames consists of the first number of frames received via the first input after receipt of the first capture signal.

10. Endoscope system according to any of the preceding items, wherein the processing device comprises a first output configured to be connected to an external image processing device, and the processing device is configured to output the designated frame via the first output.

11. Endoscope system according to item 10, wherein the external image processing device is a video grabber.

12. Endoscope system according to any of the preceding items, wherein the processing device comprises a second output, and the processing device being configured to output, via the second output, the frames received via the input.

13. Endoscope system according to any of items 10-12, wherein the processing device is configured to change from a first state to a second state after receipt of the first capture signal, wherein in the first state the processing device is configured to output, via the first output, the frames received via the input, and in the second state the processing device is configured to output, via the first output, the designated frame.

14. Endoscope system according to item 13 as dependent on item 12, wherein in the first state the processing device is configured to output, via the second output, the frames received via the input, and in the second state the processing device is configured to output, via the second output, the frames received via the input.

15. Endoscope system according to any of items 13-14, wherein the processing device is configured to change from the second state to the first state after a predetermined time after changing from the first state to the second state.

16. Endoscope system according to any of items 13-15, wherein the processing device is configured to change from the second state to the first state in response to receipt of a third capture signal, indicative of an operator performing a third action.

17. Endoscope system according to any of the preceding items, wherein the endoscope system comprises a display unit, and wherein the processing device is configured to display the designated frame via the display unit.

18. Endoscope system according to item 17, wherein the processing device is configured to display the frames received via the input concurrently with display of the designated frame.

19. Endoscope system according to any of the preceding items, wherein the one or more quality properties comprise one or more of sharpness, contrast, and noise.

20. Endoscope system according to any of the preceding items, wherein the processing device is configured to perform a Laplacian operation and/or a Laplacian of Gaussian operation to determine the one or more quality properties of each of the first plurality of frames.

21. Endoscope system according to any of the preceding items, wherein the first frame rate is between 20-40 fps, such as 30 fps.

22. Endoscope system according to any of the preceding items comprising an endoscope with an endoscope handle and an elongated flexible member extending from the endoscope handle to a distal end, wherein the image sensor is positioned at the distal end.

23. Endoscope system according to any of the preceding items, wherein the processing device is configured to store the designated frame to a memory.

24. Endoscope system according to any of the preceding items, wherein the processing device is configured to cause storing of the designated frame to an external memory.

25. A method for operating an endoscope system comprising an image sensor and a processing device, the method comprising:
consecutively receiving frames captured by the image sensor;
receiving a first capture signal, indicative of an operator performing a first action associated with capturing a still image of the frames captured by the image sensor;
storing a first plurality of frames of the frames captured by the image sensor;
determining one or more quality properties of each of the first plurality of frames; and
selecting a designated frame of the first plurality of frames based on the one or more quality properties.

26. Method according to item 25, wherein storing the first plurality of frames is performed after receipt of the first capture signal, and wherein the first plurality of frames are frames captured by the image sensor after receiving the first capture signal.

27. Method according to any of items 25-26 comprising outputting the designated frame via a first output.

28. Method according to any of items 25-27 comprising outputting the frames captured by the image sensor via a second output.

29. Method according to any of items 25-28 comprising prior to receiving the first capture signal:
outputting, via the first output, the frames captured by the image sensor; and
outputting, via the second output, the frames captured by the image sensor, after receipt of the first capture signal:
outputting, via the first output, the designated frame; and
outputting, via the second output, the frames captured by the image sensor.

The present disclosure has been described with reference to preferred embodiments. However, the scope of the disclosure is not limited to the illustrated embodiments, and alterations and modifications can be carried out without deviating from the scope of the disclosure.

Throughout the description, the use of the terms "first", "second", "third", "fourth", "primary", "secondary", "tertiary" etc. does not imply any particular order or importance, but are included to identify individual elements. Furthermore, the labelling of a first element does not imply the presence of a second element and vice versa.

LIST OF REFERENCES 2 endoscope system
4 image sensor
6 processing device
7 processing unit
8 image sensor output
10 input
12 first output
14 second output
16 capture button
18 display unit
19 memory
20 external image processing device
22 input of external image processing device
24 external display device
26 input of external display device
50 endoscope
52 endoscope handle
54 elongated member
56 distal end of elongated member
100 frames
102 first capture signal
104 second capture signal
106 third capture signal
108 first output signal
110 second output signal
200 method
202 consecutively receiving frames
203a outputting received frames, e.g. via first output
203b outputting received frames, e.g. via second output
204 receiving first capture signal
206 storing first plurality of frames
208 receiving second capture signal
210 determining one or more quality properties
212 selecting designated frame
214 outputting designated frame, e.g. via first output
216 outputting received frames, e.g. via second output

The invention claimed is:

1. An endoscope system comprising:
an image sensor comprising an image sensor output; and
a processing device comprising an input connected to the image sensor output, the processing device is configured to:
consecutively receive at a first frame rate, via the input, frames captured by the image sensor;
receive a first capture signal, indicative of an operator performing a first action associated with capturing a still image of the frames received via the input;
receive a second capture signal after receipt of the first capture signal, indicative of the operator performing a second action associated with capturing the still image of the frames received via the input;
temporarily store a first plurality of frames of the frames received via the input after receipt of the first capture signal, wherein the first plurality of frames are frames received via the input after receiving the first capture signal, wherein, in accordance with more than a first number of frames being received via the first input between receipt of the first capture signal and receipt of the second capture signal, the first plurality of frames consists of the first number of frames received via the first input immediately prior to receipt of the second capture signal, and wherein, in accordance with less than the first number of frames being received via the first input between receipt of the first capture signal and receipt of the second capture signal, the first plurality of frames consists of the first plurality of frames received via the first input after receipt of the first capture signal, the first plurality of frames including, additionally, frames received after receipt of the second capture signal;
determine one or more quality properties of each of the first plurality of frames; and
select a designated frame of the first plurality of frames based on the one or more quality properties.

2. Endoscope system according to claim 1, wherein the first action corresponds to the operator initiating a press of a capture button.

3. Endoscope system according to claim 1, wherein the first action corresponds to the operator initiating a press of a capture button, and wherein the second action corresponds to the operator releasing the press of the capture button.

4. Endoscope system according to claim 1, wherein the first number of frames comprises more than 5 frames.

5. Endoscope system according to claim 1, wherein the processing device is configured to, after selection of the designated frame of the first plurality of frames, discard the first plurality of frames except the designated frame.

6. Endoscope system according to claim 1, further comprising a display unit, wherein the processing device is configured to display the designated frame via the display unit.

7. Endoscope system according to claim 6, wherein the processing device is configured to concurrently display the frames received via the input and the designated frame.

8. Endoscope system according to claim 1, wherein the one or more quality properties comprise one or more of sharpness, contrast, and noise.

9. Endoscope system according to claim 1, wherein the processing device is configured to perform a Laplacian operation and/or a Laplacian of Gaussian operation to determine the one or more quality properties of each of the first plurality of frames.

10. Endoscope system according to claim 1, wherein the first frame rate is between 20-40 frames per second.

11. Endoscope system according to claim 1, further comprising an endoscope with an endoscope handle and an elongated flexible member extending from the endoscope handle to a distal end, wherein the image sensor is positioned at the distal end.

12. Endoscope system according to claim 1, wherein the processing device is configured to store the designated frame to a memory.

13. Endoscope system according to claim 1, wherein the processing device is configured to cause storing of the designated frame to an external memory.

14. The endoscope system of claim 1,
wherein the processing device comprises a first output configured to be connected to an external image processing device, and the processing device is configured to output the designated frame via the first output, and wherein the processing device comprises a second output, and the processing device being configured to output, via the second output, the frames received via the input.

15. Endoscope system according to claim 14, wherein the external image processing device is a video grabber.

16. Endoscope system according to claim 14, wherein the processing device is configured to change from a first state to a second state after receipt of the first capture signal, wherein in the first state the processing device is configured to output, via the first output, the frames received via the input, and in the second state the processing device is configured to output, via the first output, the designated frame.

17. Endoscope system according to claim 16, wherein in the first state the processing device is configured to output, via the second output, the frames received via the input, and in the second state the processing device is configured to output, via the second output, the frames received via the input.

18. Endoscope system according to claim 16, wherein the processing device is configured to change from the second state to the first state after a predetermined time after changing from the first state to the second state.

19. Endoscope system according to claim 16, wherein the processing device is configured to change from the second state to the first state in response to receipt of a third capture signal, indicative of an operator performing a third action.

20. Endoscope system according to claim 14, wherein the processing device is configured to change from a first state to a second state after receipt of the first capture signal, wherein in the first state the processing device is configured to output, via the first output, the frames received via the input, and in the second state the processing device is configured to output, via the first output, the designated frame.

* * * * *